(12) United States Patent
Lewis, Jr.

(10) Patent No.: US 10,777,322 B2
(45) Date of Patent: Sep. 15, 2020

(54) PATIENT CENTRIC DRUG ANALYSIS PLATFORM

(71) Applicant: Lewis Pharmaceutical Information, Inc., Jasper, TN (US)

(72) Inventor: James Morgan Lewis, Jr., Jasper, TN (US)

(73) Assignee: LEWIS PHARMACEUTICAL INFORMATION, INC., Jasper, TN (US)

( * ) Notice: Subject to any disclaimer, the term of this patent is extended or adjusted under 35 U.S.C. 154(b) by 0 days.

(21) Appl. No.: 16/559,911

(22) Filed: Sep. 4, 2019

(65) Prior Publication Data

US 2020/0027562 A1    Jan. 23, 2020

Related U.S. Application Data

(63) Continuation of application No. 16/185,151, filed on Nov. 9, 2018.

(60) Provisional application No. 62/699,065, filed on Jul. 17, 2018.

(51) Int. Cl.
*G16H 50/20* (2018.01)
*G16H 10/60* (2018.01)

(52) U.S. Cl.
CPC ............. *G16H 50/20* (2018.01); *G16H 10/60* (2018.01)

(58) Field of Classification Search
None
See application file for complete search history.

(56) References Cited

U.S. PATENT DOCUMENTS

| 8,688,477 B1* | 4/2014 | Huizenga | G06F 19/3475 |
| | | | 705/3 |
| 2006/0287906 A1 | 12/2006 | McGillin | |
| 2008/0004899 A1* | 1/2008 | Braxton | G06F 19/3481 |
| | | | 705/2 |
| 2008/0082351 A1* | 4/2008 | Kelley-Hrabe | G06Q 50/22 |
| | | | 705/2 |
| 2008/0294459 A1* | 11/2008 | Angell | G16H 50/20 |
| | | | 705/2 |

(Continued)

OTHER PUBLICATIONS

International Search Report and Written Opinion dated Oct. 1, 2019 for corresponding PCT Application No. PCT/US2019/041523.

*Primary Examiner* — Michael Tomaszewski
*Assistant Examiner* — Jay M. Patel
(74) *Attorney, Agent, or Firm* — Polsinelli PC

(57) ABSTRACT

The present disclosure relates to a patient centric system and platform that enables a customized analysis of a patient's health conditions for assessing appropriateness of an ordered treatment. In one aspect, patient centric analysis platform includes memory having computer-readable instructions stored therein and one or more processors. The one or more processors configured to execute the computer-readable instructions to receive, from a terminal, patient identifying information of a patient; receive, from the terminal, an initial treatment order for the patient; retrieve patient specific information and treatment specific information; generate a numerical assessment of the initial treatment order based on the patient specific information and the treatment specific information, the numerical assessment indicating a safety level of the initial treatment order; and communicate the numerical assessment to the terminal.

20 Claims, 7 Drawing Sheets

(56) References Cited

U.S. PATENT DOCUMENTS

| | | | |
|---|---|---|---|
| 2008/0294507 A1 | 11/2008 | Reiner | |
| 2011/0112970 A1* | 5/2011 | Yu | G06Q 10/10 |
| | | | 705/51 |
| 2012/0122870 A1* | 5/2012 | Smith | A61K 31/133 |
| | | | 514/236.8 |
| 2012/0253771 A1* | 10/2012 | Col | G16H 50/50 |
| | | | 703/11 |
| 2013/0247193 A1* | 9/2013 | Zaitsev | G06F 21/552 |
| | | | 726/23 |
| 2014/0221490 A1* | 8/2014 | Lacouture | A61P 25/04 |
| | | | 514/567 |
| 2014/0350369 A1* | 11/2014 | Budiman | G06F 19/3456 |
| | | | 600/365 |
| 2014/0358576 A1* | 12/2014 | Hoffman | G06F 19/00 |
| | | | 705/2 |
| 2016/0232321 A1* | 8/2016 | Silverman | G16H 10/60 |
| 2016/0331244 A1* | 11/2016 | Barton-Sweeney | A61B 5/024 |
| 2018/0016318 A1* | 1/2018 | Alsina-Fernandez | |
| | | | C07K 14/57509 |

\* cited by examiner

PATIENT CENTRIC DRUG ANALYSIS PLATFORM

PRIORITY INFORMATION

This application claims priority to and is a continuation of U.S. patent application Ser. No. 16/185,151, filed on Nov. 9, 2018, which claims the benefit under 35 U.S.C. § 119(e) of the filing date of U.S. Provisional Application No. 62/699,065, filed on Jul. 17, 2018, entitled "PATIENT CENTRIC AND DRUG ADMINISTRATION ASSISTANCE PLATFORM", the entire content of which is incorporated herein by reference.

BACKGROUND

With healthcare costs constantly on the rise and the debate around controlling it never ending, officials and healthcare professionals have yet to present a sustainable solution to this problem. While all sides of this debate spend their time and energy on debating ancillary solutions such as tax hikes, cuts to services, etc., to reduce healthcare costs, none address root causes of healthcare costs.

The most effective way of controlling or reducing healthcare costs is to reduce likelihood of health problems from arising in the first place. In doing so, proper analysis of health issues and proper drug or treatment administration regimens can prevent health issues from being prolonged, which in turn can reduce various long term consequences and associated costs of healthcare including hospital admissions, stays, medical surgeries, additional drug administrations, etc.

Furthermore, no two individual's healthcare conditions are the same and thus using uniform guidelines and medical databases for proper drug administration is inefficient. Accordingly, a customized analysis of a patient that takes into consideration each individual's personalized health state and history is needed.

BRIEF DESCRIPTION OF THE DRAWINGS

In order to describe the manner in which advantages and features of the disclosure can be obtained, a more particular description of the principles briefly described above will be rendered by reference to specific example embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

SUMMARY

Figure 1:
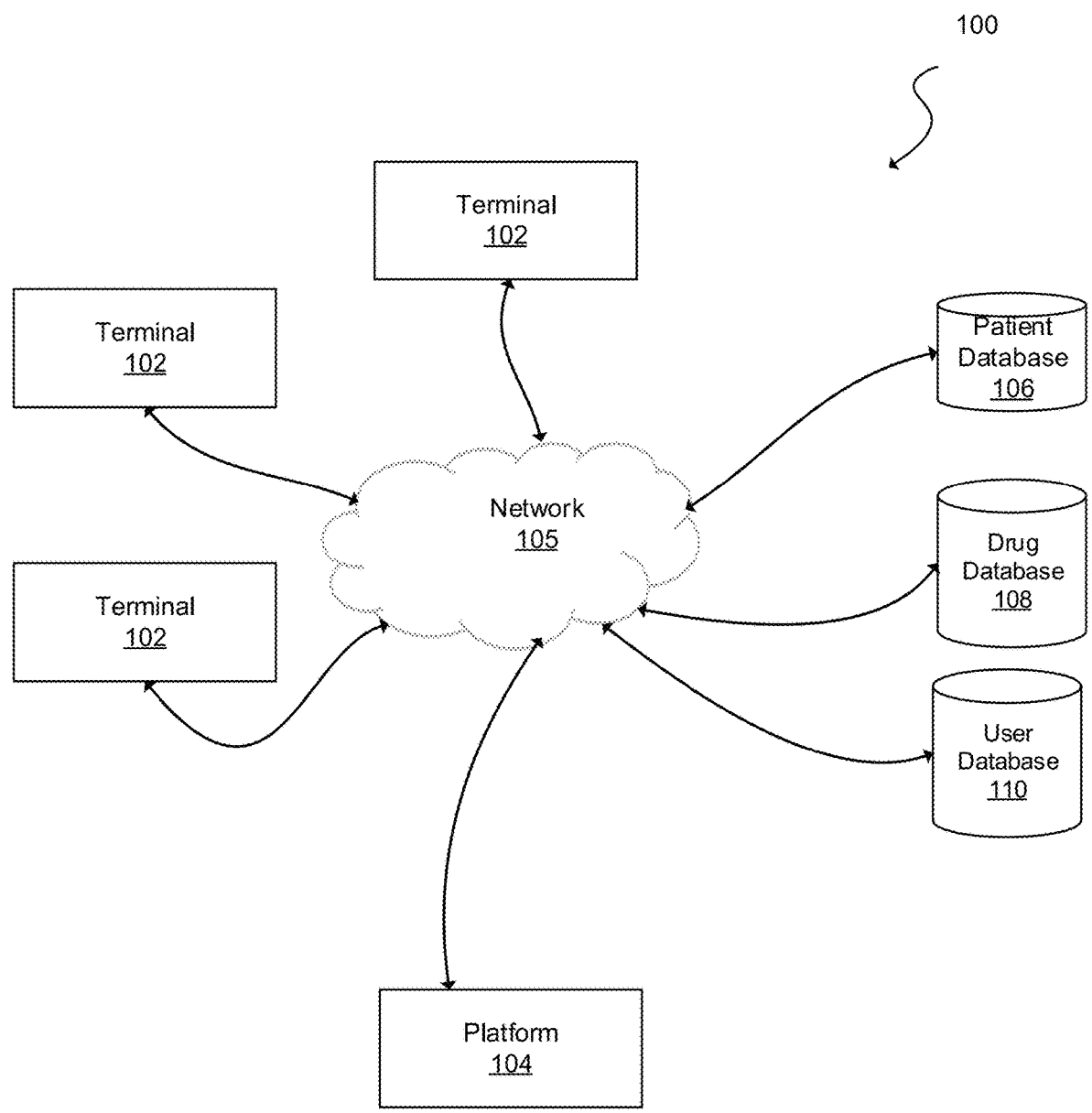
FIG. 1 is an example of a system including a patient and drug assistance platform, according to one aspect of the present disclosure.

Aspects of the present disclosure are directed to a platform that is accessible to physicians, pharmacists, care providers and/or patients, that can receive patient identifying information and an initial ordered dosage of a particular medication or treatment as input, access various patient specific and treatment related information, perform an analysis on the patient specific and treatment related information to generate a personalized relative safety score for a particular patient, and present on a graphical user interface through which the platform is accessed, the relative safety score as well as a detailed analysis of the patient related information. This information can then be used by the physician, pharmacist, care provider or the patient to make a decision on proceeding with the initial ordered dosage, modify the dosage and/or modify the initially ordered treatment/medication and corresponding dosage.

In one aspect, a patient centric analysis platform includes memory having computer-readable instructions stored therein and one or more processors. The one or more processors configured to execute the computer-readable instructions to receive, from a terminal, patient identifying information of a patient; receive, from the terminal, an initial treatment ordered for the patient; retrieve patient specific information and treatment specific information; generate a numerical assessment of the initial treatment order based on the patient specific information and the treatment specific information, the numerical assessment indicating a relative safety level of the initial treatment order; and communicate the numerical assessment to the terminal.

In one aspect, patient centric analysis method includes receiving, from a terminal, patient identifying information of a patient; receiving, from the terminal, an initial treatment order for the patient; retrieving patient specific information and treatment specific information; generating a numerical assessment of the initial treatment recommendation based on the patient specific information and the treatment specific information, the numerical assessment indicating a relative safety level of the initial treatment order; and communicate the numerical assessment to the terminal.

In one aspect, one or more non-transitory computer-readable media have computer-readable instructions stored thereon, which when executed by one or more processors, cause the one or more processors to receive, from a terminal, identifying information of a patient; receive, from the terminal, an initial treatment order for the patient; retrieve patient specific information and treatment specific information; generate a numerical assessment of the initial treatment order based on the patient specific information and the treatment specific information, the numerical assessment indicating a relative safety level of the initial treatment order; and communicate the numerical assessment to the terminal.

DETAILED DESCRIPTION

Various example embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an example embodiment in the present disclosure can be references to the same example embodiment or any example embodiment; and, such references mean at least one of the example embodiments.

Reference to "one embodiment" or "an embodiment" means that a particular feature, structure, or characteristic described in connection with the embodiment is included in at least one example embodiment of the disclosure. The appearances of the phrase "in one embodiment" in various places in the specification are not necessarily all referring to the same example embodiment, nor are separate or alternative example embodiments mutually exclusive of other example embodiments. Moreover, various features are described which may be exhibited by some example embodiments and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various example embodiments given in this specification.

Without intent to limit the scope of the disclosure, examples of instruments, apparatus, methods and their related results according to example embodiments of the present disclosure are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Disclosed are various non-limiting examples of a platform that provides a patient centric analysis of a patient's health conditions coupled with a corresponding numerical value for a treatment/medication dosage to be administered. The disclosure begins with an example system.

FIG. 1 is an example of a system including a patient and drug assistance platform, according to one aspect of the present disclosure. System 100 includes one or more terminals 102 that can be accessed by a physician, a pharmacist, a user, etc. Terminals 102 can be any known or to be developed terminal including, but not limited to, a mobile device, a tablet, a desktop computer, etc., each of which may have a Graphical User Interface (GUI) for a user to access system 100 therethrough.

System 100 further includes platform 104. Platform 104 can be cloud based residing on any known or to be developed public, private and/or a hybrid cloud provided by a cloud service provider.

Communications between platform 104 and terminals 102 can be according to any known or to be developed wired and/or wireless communication method, using network 105. Platform 104 can have one or more processors and memories that include computer-readable instructions. The one or more processors can execute the computer-readable instructions to perform functionalities of platform 104, as will be described below. Components of platform 104 and/or terminals 102 will be further described below with reference to FIG. 6.

Terminals 102 can be used to log in to system 100 and access platform 104 using any known or to be developed authentication method (e.g., by providing a username and a password, using a multi-step authentication process, etc.).

System 100 further includes one or more public and/or private databases, with which it can communicate, via known or to be developed wired and/or wireless communication method using network 105, to store and/or retrieve information as will be described below.

One example of such database includes patient database 106, which can have stored thereon, various patient specific information including, but not limited to, a patient profile that identifies the patient, drug usage history of the patient, current mediations and treatments the patient is on or going through, etc. Patient identification information can include, but is not limited to, height, weight, age, sex, disease states, allergies, pregnancy information, symptoms and critical labs results, antibiotic therapy duration, clinical abuse/misuse of medications, etc.

Another example of such databases is drug database 108, which can have stored therein, various types of data about a specific treatment or drug including, but not limited to, a drug's classification, a drug's interaction with other drugs, metabolic pathway interactions of a drug, drug-disease interaction for a drug, renal functionality effect of a drug, allergy related information of a drug, etc. This data may be pulled from or updated based on information provided by manufacturers of such treatments/drugs, publicly available statistics and research results, etc. Furthermore, any updated findings on existing drugs/treatments (obtained through various trials or academic research) as well as information on new drugs introduced into the market may be added to drug database 108. Accordingly, drug database 108 may be updated periodically.

Another example database is user database 110. Each user, whether it is a physician, pharmacists, care provider, a patient, a healthcare provider, etc., may register with system 100 for access to platform 104. Accordingly, each such user may have a profile with system 100 that is stored and maintained at user database 110.

While FIG. 1 illustrates two example databases 106 and 108, each having a number of particular information stored therein, the present disclosure is not limited thereto. For example, information listed above as examples of data stored in drug database 108 may be stored in two or more separate databases. Similarly, information listed above as examples of data stored in patient database 106 may be stored in two or more separate databases.

Furthermore, while FIG. 1 illustrates a particular number of certain components, the present disclosure is not limited thereto. For example, number of terminals 102 is not limited to three as shown platform 104 may be residing on more than one cloud provider, etc. Furthermore, system 100 can include any additional number of components for proper functioning thereof including but not limited to, routers, access points, etc.

Figure 2:
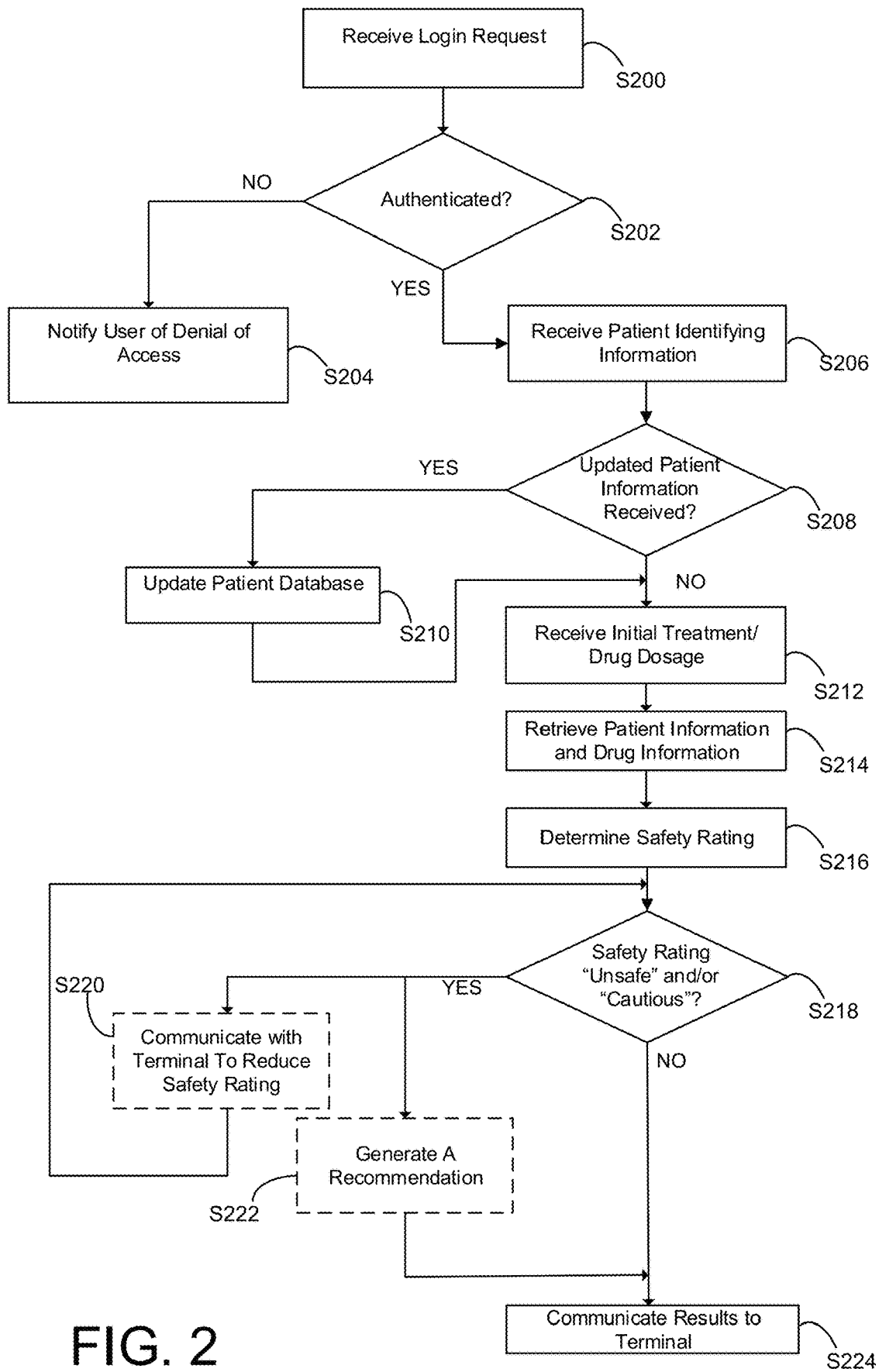
FIG. 2 is a method of providing patient centric analysis and drug administration recommendations, according to one aspect of the present disclosure.

FIG. 2 is a method of providing patient centric analysis and drug administration recommendations, according to one aspect of the present disclosure. FIG. 2 will be described from the perspective of platform 104. However, it will be understood that, as noted above, platform 104 may have one or more processors/servers, associated therewith that execute computer-readable instructions (stored on one or more associated memories) to perform steps of FIG. 2.

At S200, platform 104 may receive a login request from one of terminals 102 (terminal 102). The request login request may be received from a doctor, a pharmacist, a care provider, a patient, a healthcare agency administrator or operator, etc. (all of whom may be referred to as users, hereinafter). Each user may have registered with system 100 and have a corresponding profile with corresponding identifying information stored in a database such as user database 110. At the time of registration, each user may be assigned a username and password for the user to use at terminal 102 at step 300 as part of the login request. In one example, while the login request may be received from one of terminals 102, two or more of terminals 102 may operate on the same network and thus platform 104 may be subsequently accessed from any one or more connected ones of terminals 102. In another example, login to platform 104 may be requested (e.g., simultaneously) from more than one of terminals 102 using same or different credentials (same or different username/password)

At S202, platform 104 may process the login request received at S200. In other words, platform 104 may validate/authenticate corresponding login information (e.g., a username and password) provided by the requesting party at S200. If the login request cannot be authenticated, a message will be sent to terminal 102 notifying the user of the denial of access at S204. If authenticated, the process proceeds to S206.

At S206, platform 104 may receive patient identifying information, which can include a patient's name, date of birth, social security number, etc.

S208, platform 104 may determine if any updated patient related health information is received via one or more of terminals. This updated information may be input via a GUI on one or more of terminals 102 by a user of terminal 102. This information may include any health related conditions, updates communicated to the user of terminal 102 by the patient such as recent medications being taken, a recent (not reported) health condition, effects, etc. This information can include patient's height, weight, age, sex, diagnosis, allergies, kidney function, liver function, DNA make-up, and possible drug interactions.

If updated patient related information is received at S208, then at S210, platform 104 updates a corresponding patient profile stored in patient database 106 (or generates a new one for a new patient) and the process then proceeds to S212. If updated patient related information is not received at S208, the process proceeds to S212.

At S212, platform 104 may receive, from one or more terminals 102, an initial dosage of treatment/drug for the patient, which may also be referred to a preliminary drug order or an initial treatment order to be prescribed for the patient. For example, such initial dosage may be 20 mg of Prozac to be taken once a day for a period of 30 days.

At S214, platform 104 may retrieve patient related information and drug/treatment information from patient database 106 and drug database 108, respectively.

At S216 and based on the initial dosage, the patient information and the drug/treatment information, platform 104 may run an algorithm to generate a Patient Profile Relative Safety Rating or a patient safety rating for the patient (this may also be referred to as a patient safety score or a numerical assessment). In one example, this rating may have a numerical value that can range from 0 to 100. In another example, there may be no upper limit on the numerical value of the patient safety rating for a given patient. Platform 104 may set thresholds for "safe," "cautious," "unsafe" ratings. For example, a safety rating of less than 25 is relatively "safe" while a rating above 50 is relatively not safe. In another example, a safety rating of 0-25 is relatively safe, while added caution may be advised as the score approaches 50 and above 50 may be considered relatively "unsafe". Designation of a range for the safety score to be considered safe or not, is not limited to this example but may be set differently by an operator of platform 104 based on experiments and/or empirical studies.

At S218, platform 104 may determine if the safety rating of S216 is "unsafe" or "cautious"/"unsafe". If "unsafe" or "cautious"/"unsafe," platform 104 may optionally perform the process of S220 and/or S222. Alternatively, platform 104 may skip S220 and S222 and proceed straight to S224, as will be described below.

At S220, platform 104 may communicate with terminal 102 to determine if the safety rating can be reduced. For example, therapeutic duplications (an example of an adverse effect) can increase the safety rating score. Therefore, for an "unsafe" rating, platform 104 can recommend to user of terminal 102 (or the user can instruct platform 104) to eliminate the therapeutic duplications from consideration in determining the safety rating. In response to communication at S220 and the feedback received from a user via a corresponding one of terminals 102, platform 104 repeats S216 to recalculate/update safety rating. Then, S216, S218 and S220 may be repeated until safety rating determined at S216 is "safe."

As an alternative to S220 (or in conjunction with S220), at S222, platform 104 may automatically determine a different dosage of the same treatment/drug (relative to the initially ordered dosage receive at S212 to the user at the corresponding terminal 102 or determine an alternative treatment/drug at the initially ordered dosage or at an alternative dosage by analyzing various patient specific information retrieved from patient database 106 and/or treatment/drug factors retrieved from drug database 108.

In one example, at S222, platform 104 may generate a recommendation that can include a list of possible drugs to be administered to the patient together with a recommended dosage. In one example and with each drug and suggested dosage, platform 104 also generates a daily, weekly, monthly and yearly cost savings report, a drug interaction report and adverse reaction report, etc.

At S224, platform 104 communicates results to the user at a corresponding one of terminals 102. The results may include the safety rating, a list of drugs, recommended dosages and/or the reports to the user on the corresponding one of terminals 102. Examples of a GUI through which information may be exchanged with the user on the corresponding terminal 102 will be described with reference to FIGS. 4 and 5.

In one example and when user of terminal 102 has provided an initial suggestion of a drug (and/or associated dosage), platform 104 can either confirm the initial suggestion at S224 and communicate the same to terminal 102 or, based on the safety rating, suggest an appropriate dose to the prescriber (user of terminal 102). at S224.

Figure 3:
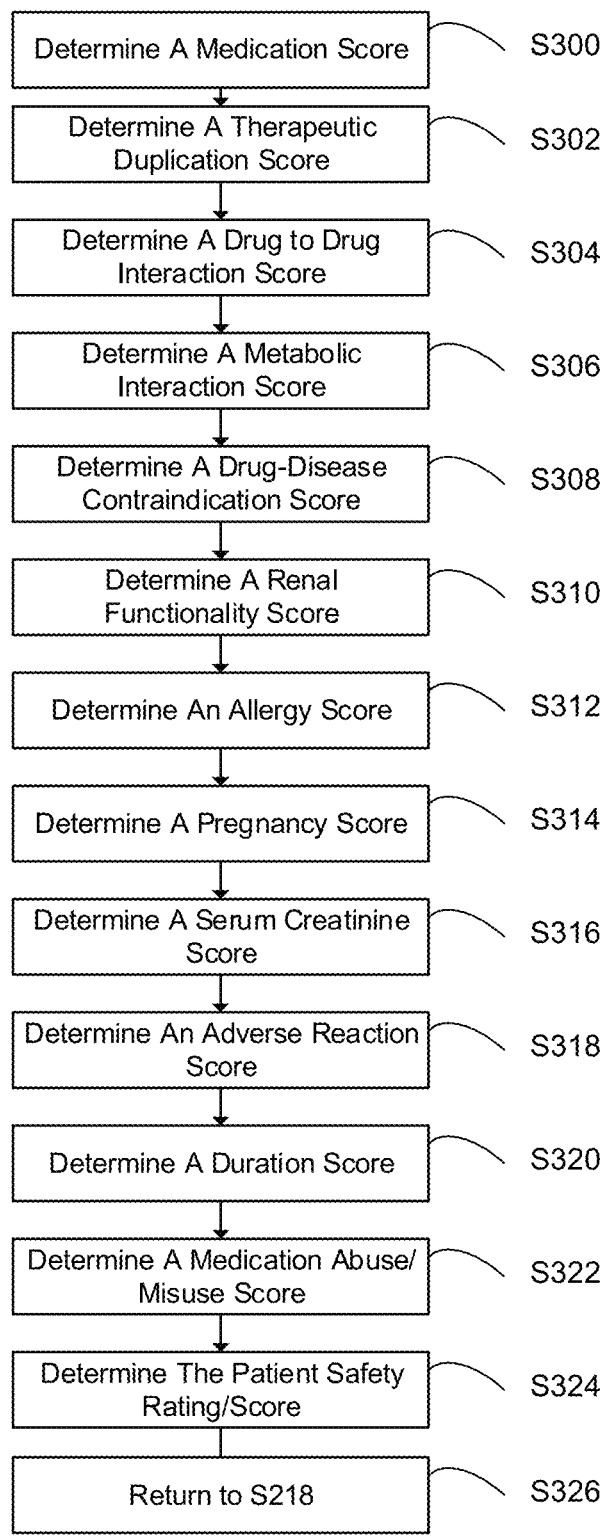
FIG. 3 is a method of determining a patient safety rating, according to one aspect of the present disclosure.

FIG. 3 is a method of determining a patient safety score, according to one aspect of the present disclosure. FIG. 3 will be described from the perspective of platform 104. However, it will be understood that, as noted above, platform 104 may have one or more processors/servers, associated therewith that execute computer-readable instructions (stored on one or more associated memories) to perform steps of FIG. 3.

At S300, platform 104, based on patient identifying information, patient information and initial treatment/drug dosage received at S206, S208 and S210, may determine a medication score. For example, each medication at a recommended starting dose is assigned a score of 1. A Dose Multiplier may indicate a percentage of the recommended dose for the treatment/drug. A formula for calculating the medication's score may be given as [Recommended Dose Score*Multiplier*Doses per Day]. For example, a recommended starting dose for Prozac (fluoxetine) may be 20 mg once daily but the initial dosage received at platform 104 at S212 for Prozac (fluoxetine) may be 10 mg (0.5 or half of the recommended dosage) once daily. Therefore, the medication score may be given by [Recommended Dose Score (1)*Multiplier (0.5)*Doses per Day (1)]=[1*0.5*1]=0.5. In another example, the initial dosage received at platform 104 at S212 for Prozac (fluoxetine) may be 20 mg two times daily. Therefore, the medication score may be given by [Recommended Dose Score (1)*Multiplier (1)*Doses per Day (2)]=[1*1*2]=2.

At S302, platform 104 may determine a therapeutic duplication score for the initial treatment/drug. Each therapeutic classification duplication score may be assigned a score of 1. As an example. Diazepam is classified as a benzodiazepine. Temazepam is also classified as a benzodiazepine. If both medications are ordered for the same patient, platform 104 assigns a therapeutic duplication score of 1 for Diazepam and benzodiazepine. In another example, Chlordiazepoxide is also classified as a benzodiazepine. If Chlordiazepoxide is also ordered on this same patient, platform 104 assigns a therapeutic duplication score of 2 for Diazepam, benzodiazepine and Chlordiazepoxide. Therapeutic Duplication (TD) score may be determined as follows: 1 point for each drug in the same therapeutic classification. In other words, TD Score=[[TD Drug #1]*(TD Drug #2+TD Drug #3+TD drug #4, etc.)].

At S304, platform 104 may determine a drug to drug interaction score for the initial treatment/drug. When a medication at an initially recommended starting dose is ordered once daily and is identified as having an adverse interaction with another medication also ordered at a recommended starting dose once daily, the drugs are identified and an interaction score of 1 is assigned to each ordered drug. If the same medication at ordered starting dose interacts adversely with another ordered medication at recommended starting dose that interaction is also assigned a score of 1.

In one example. Coumadin (warfarin) has a recommended starting dose of 5 mg once daily. Prozac (fluoxetine) has a recommended starting dose of 20 mg once daily. There may be a documented adverse reaction between Coumadin (warfarin) and Prozac (fluoxetine). If there is an order for Coumadin (warfarin) 5 mg once daily and Prozac (fluoxetine) 20 mg once daily for the patient, platform 104 determines the drug to drug interaction score using [[Recommended Starting Dose Score*Multiplier]*[Doses per Day]] for Drug #1)*[[Recommended Starting Dose Score*Multiplier]*[Doses per Day]] for Drug #2)]=Drug-Drug Interaction Score, as a formula. In this particular example, using the above formula results in a drug to drug interaction score of 1 for Coumadin and Prozac ([1*1*1] for Coumadin (warfarin)*[1*1*1] for Prozac (fluoxetine)=1).

In another example, Coumadin (warfarin) has a recommended starting dose of 5 mg once daily. Prozac (fluoxetine) has a recommended starting dose of 20 mg once daily. There is a documented adverse reaction between Coumadin (warfarin) and Prozac (fluoxetine). If there is an order for Coumadin (warfarin) 10 mg once daily and Prozac (fluoxetine) 20 mg twice daily for the patient, using the above formula results in a drug to drug interaction score of 4 for Coumadin and Prozac ([1*2*1] for Coumadin (warfarin)*[1*1*2] for Prozac (fluoxetine)=4).

At S306, platform 104 may determine a metabolic interaction score for the initial treatment/drug. When a medication is approved by the Food and Drug Administration (FDA) for treatment of a disease or a condition, the manufacturer is typically required to divulge pertinent information about that medication. One example of such pertinent information is how the medication is metabolized by the patient's body. When medications have been in use for many years, the experience with thousands or millions of doses in many different situations, drug interactions are discovered and documented over time, which may be retrieved and stored in database 108. With respect to newer or more recent medications, where such data is not readily available, the actions of the metabolic pathways on those medications yield clues as to potential interactions that may not be documented.

For example, if Drug #1 is metabolized mainly by the Cytochrome P 3A4 (CYP 3A4) pathway in the liver and Drug #2 is an strong inhibitor of that CYP 3A4 pathway, the chances of an adverse effect from Drug #1 are enhanced and should be noted. The formula for the metabolic interaction score may be the same as the formula described above for the drug to drug interaction score (e.g., [[Recommended Starting Dose Score*Multiplier]*[Doses per Day]] for Drug #1)*[[Recommended Starting Dose Score*Multiplier]*[Doses per Day]] for Drug #2)]=Drug-Drug Interaction Score).

At S308, platform 104 may determine a drug-disease contraindication score for the initial treatment/drug. Patients sometimes develop symptoms or medical emergencies which might cause a current medication to be dangerous for the patient. For example, a patient may be bleeding profusely or hemorrhaging. As a result, the patient may have been taking Coumadin (warfarin) which is a blood thinner. Unless the patient stops taking his Coumadin (warfarin) in this situation, the end result may be the death of the patient. This is referred to as a Drug-Disease Contraindication. Accordingly, platform 104 may examine the patient's symptoms and medications available in patient database 106 to find such disease conditions and warn about such contraindications. Each incident of drug-disease Contraindication may be assigned a score of 2 points by platform 104.

In another example, any positive value for the drug-disease contraindication or alternatively, a positive value above a threshold, may result in a generation of a message such as a "do not administer" message to the corresponding user/physician/pharmacist/healthcare provider, etc.

At S310, platform 104 may determine a renal functionality score for the initial treatment/drug. When a medication which is eliminated via kidneys is ordered for a patient, frequently the standard dose for a particular disease becomes an overdose if the condition of the patient's kidneys is poor. As part of drug database 108 or any other external database, platform 104 may access renal function tables which provide information on suggested dosages of different medications appropriate for the patient's renal function. If the dose of the ordered drug/medication is not appropriately adjusted, platform 104 assigns a score of 1 for each dose calculated to be inappropriate for the patient's kidney (renal) function.

At S312, platform 104 may determine an allergy score for the initial treatment/drug. A patient may list medications to which he or she is allergic, which may be recorded in patient database 106. The fact that medications may be branded under several different names makes it possible for these medications which cause allergic reactions to be added to a patient's profile and endangering the patient. Accordingly, platform 104 examines the patient's information from patient database 106 and drug information from drug database 108 for allergies under all possible brand names to alert patients and prescribers to the danger. Each medication listed as one to which the patient is allergic is found in the patient's active medications will be assigned a score of 5 by platform 104.

At S314, platform 104 may determine a pregnancy score for the initial treatment/drug. This score may be determined if feedback is received (e.g., via terminal 102 and as part of updated patient information at S208. While active pregnancy information is provided, in another example, information is provided on whether female patients are of child bearing age. Pregnancy can complicate medication prescription because many medications can be dangerous to the unborn child. If the answer to active or child bearing age of a female patient is yes, platform 104 may assign a score of 2 points for the pregnancy score.

At S316, platform 104 may determine a Serum Creatinine score for the initial treatment/drug. This value may only be used for patients in institutions which have access to regular laboratory services. Not having a Serum Creatinine for more than seven days may result in platform 104 to assign a score of 1 for Serum Creatinine score. When an updated lab report for Serum Creatinine is reported, platform 104 may remove the Serum Creatinine score (change it back to 0).

At S318, platform 104 may determine an adverse reaction score for the initial treatment/drug. When a patient is seen by a physician or physician's assistant, a history may be compiled listing all the patient's symptoms, vital signs, laboratory results and medications. Frequently, the most likely adverse effects of some of the patient's medications may match the symptoms the patient displays. Platform 104 may scans for the most likely adverse effects of each of the patient's medications and reports matches to the patient's symptoms and diagnoses. Each instance of a medications adverse reaction matching patient symptoms or diagnoses results in platform 104 adding 2 points to the adverse reaction score.

At S320, platform 104 may determine a duration score for the initial treatment/drug. This score may be based on considering inappropriate length of a medication (e.g., antibiotic use). It has been established that overuse of antibiotics has created bacterial resistance making antibiotics less effective. This may be a physician/staff reported item, based on monitoring of antibiotic use. This score is based on the judgement of the staff and may range up to one point for every day of each antibiotic use beyond that considered necessary according to the particular underlying use case.

At S322, platform 104 may determine a medication abuse/misuse score for the initial treatment/drug. This score may also be a staff judgement call. This score may be relevant because it is one of the factors mandated by the OBRA '90 (Omnibus Budget Reconciliation Act of 1990 (which was actually passed in 1992). OBRA '90 made pharmacists personally liable for counseling patients on their medications. Evidence of clinical abuse or misuse of medications is one of the factors to be considered in counseling patients. Such report, available as part of patient information in database 106, may result in platform assigning 2 points to the medication abuse/misuse score.

At S324, platform 104 may add all the scores determined at S300 to S322 to provide a patient safety rating/score. Thereafter, at S326, the process returns to S218 of FIG. 2.

While a simple addition of all the scores described above is provided as an example of determining the patient safety rating score, the present disclosure is not limited thereto. For example, instead of an addition, platform 104 may use a weighted average or a weighted combination of all the scores where some are weighted more heavily than others (e.g., pregnancy score may be weighted higher relative to Serum Creatinine score).

Furthermore, types of particular scores that can be determined based on various available patient specific or drug specific information, as described above, are not limited to the examples described above but may include scores related to any other known or to be developed information that may have an effect of the patient if a treatment or drug is prescribed.

Figure 4:
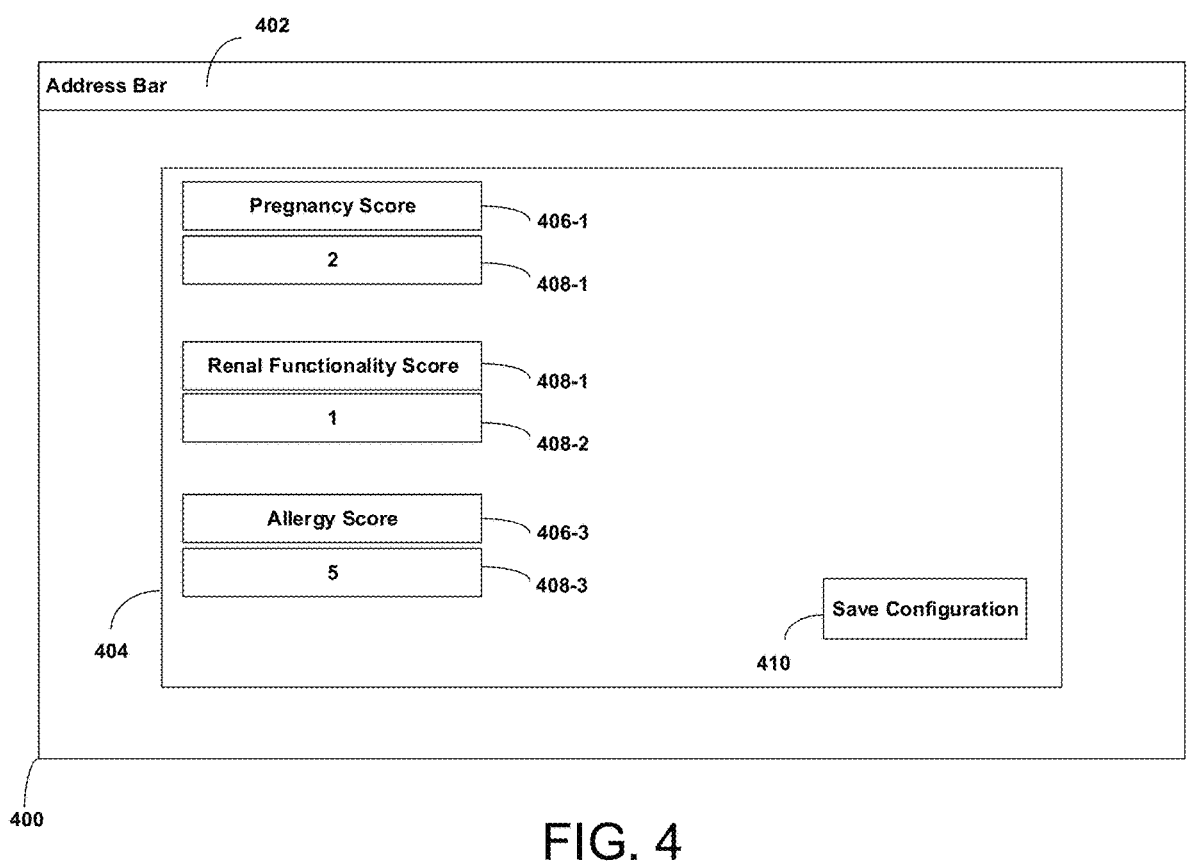
FIG. 4 illustrates an example snapshot of a configuration screen through which points assigned to each score may be adjusted, according to one aspect of the present disclosure.

In one example, point configuration by which platform 104 assigns points to various scores described above with reference to FIG. 3 may be manually adjusted by an operator accessing platform 104 via a terminal such as one of terminals 102. FIG. 4 illustrates an example snapshot of a configuration screen through which points assigned to each score may be adjusted, according to one aspect of the present disclosure.

FIG. 4 shows screen 400 which may be a GUI accessed upon entering a corresponding URL in address bar 402. In response to entering the corresponding URL, an operator of platform 104 may access configuration settings 404, which may have displayed therein particular scores such as those described above with reference to FIG. 3. Configuration settings 404 include a couple of the specific scores described with reference to FIG. 3 instead of all of them, for sake of brevity. However, it will be understood that all such scores that are within the scope of the present disclosure may have a corresponding configuration identifier and modifiable parameter included in configurations setting 404.

In the particular and non-limiting example of FIG. 4, configurations setting 404 includes identifiers 406-1, 406-2 and 406-3 of pregnancy score, renal functionality score and allergy score, described above with reference to FIG. 3. Under each one of identifiers 406-1, 406-2 and 406-3, there may be a corresponding data entry field such as data entry fields 408-1, 408-2 and 408-3.

In describing FIG. 3, particular example points are described that may be assigned to each particular score, assuming the applicable conditions exist. For example, in determining pregnancy score at S314, if the patient is a female who is pregnant and/or of child bearing age, platform 104 assigns 2 points to the pregnancy score. The particular number of points (e.g., 2 points) may be adjusted using configurations setting 404, whereby number 2 may be modified to a different number (e.g., 1 or 3) using data entry field 408-1, for example. Similar changes may be made to any other one of renal functionality and allergy scores using configurations setting 404 or any other score for which the corresponding assigned points may be configured. The changes may then be applied/saved by clicking on save configuration button (e.g., virtual button) 410.

Figure 5A:
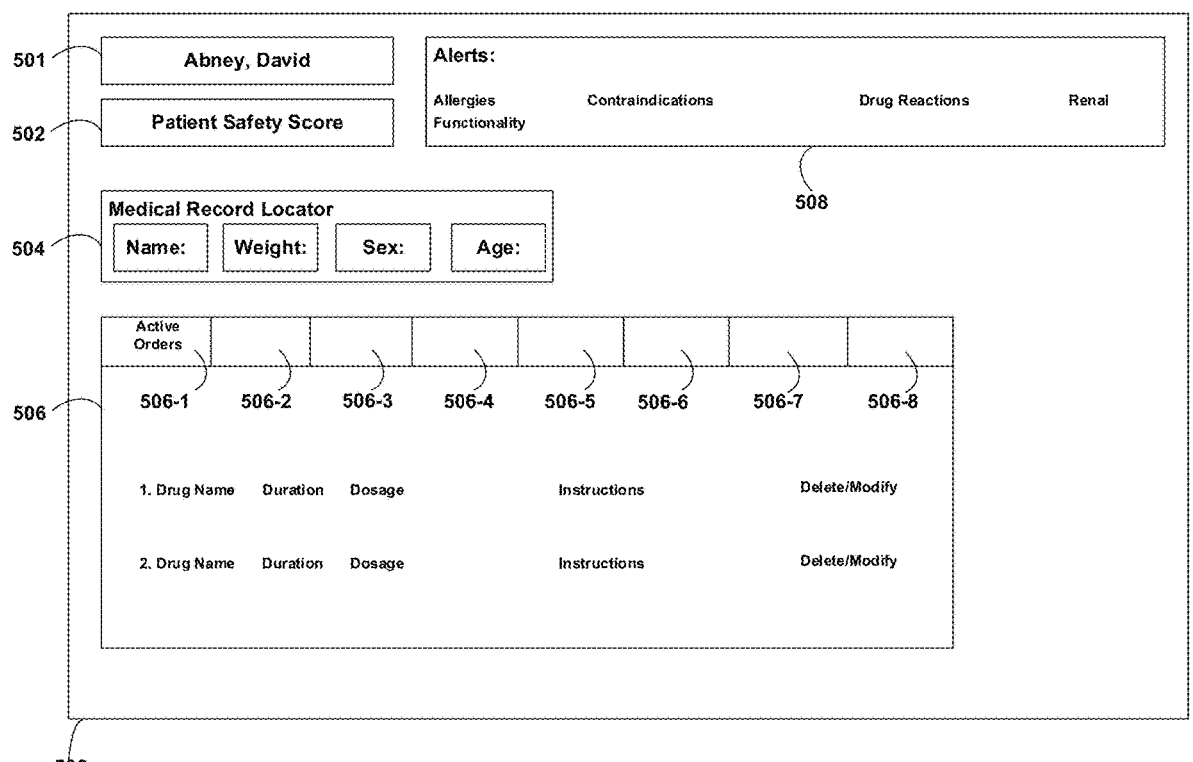
FIGS. 5A-B illustrate example screenshots of graphical user interfaces on a terminal of system of FIG. 1 displaying results of analysis of platform of FIG. 1, according to an aspect of the present disclosure.
Figure 5B:
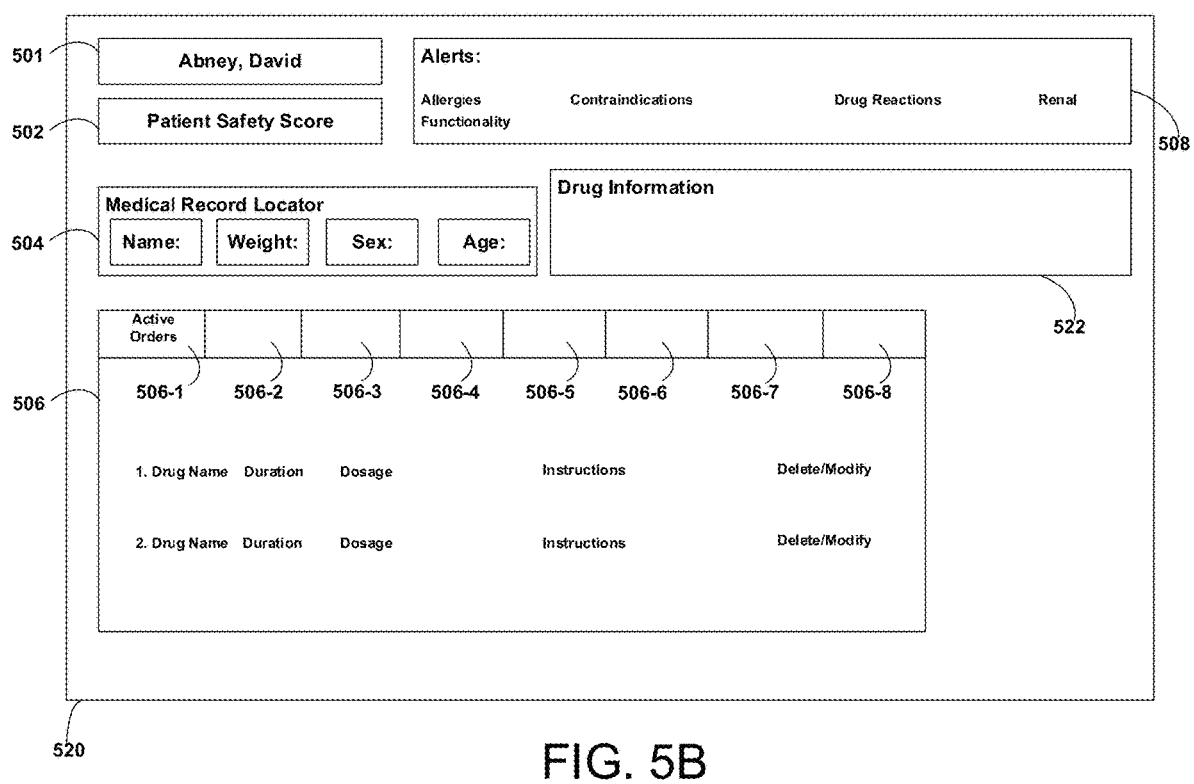

FIGS. 5A-B illustrate example screenshots of graphical user interfaces on a terminal of system of FIG. 1 displaying results of analysis of platform of FIG. 1, according to an aspect of the present disclosure.

FIG. 5A illustrates an example GUI 500 through which a user at a given one of terminals 102 can view and interact with platform 104 to receive a comprehensive report of the patient and the corresponding profile safety score for a particular treatment/drug.

GUI 500 may be accessible via a browser by typing a corresponding URL in an address bar of the browser. GUI 500 may be a dashboard that displays patient identifier 501 about a particular patient (e.g., a hypothetical patient named David Abney) and a corresponding profile safety rating 502. Furthermore, GUI 500 includes a portion 504 (medical record locator portion 504) with various identifying information for the patient (e.g., David Abney) including, but not limited to the patient's height, weight, patient ID, etc. GUI 500 also includes a portion 506 having various tabs (e.g., tabs 506-1 to 506-8) that provide to a physician, a pharmacist, etc. patient detailed information corresponding to the patient's personal conditions, health history, etc. Examples of such information include a list of active orders (currently being taken by the particular patient) including duration, dosage, any corresponding relevant information, instructions, etc. Other examples of patient detailed information shown under one of tabs 506-1 to 506-8 include, but are not limited to a patient's adverse reactions to drug intakes, contraindications, allergies, drug interactions, renal dosing adjustments, therapeutic duplications, etc.

In the particular example tab showing active orders of the patient, options may be provided for adjusting any one of the active orders, canceling any one such active order, etc.

GUI 500 also illustrates example alert portion 508, which may provide the user accessing GUI 500 with alerts regarding patient's conditions such as allergies, contraindications, drug reactions, renal functionality, etc.

While not shown, GUI 500 may also include an interactive field, whereby when the patient's profile safety score for a suggested treatment/drug is relatively "unsafe" or "cautious", the user at GUI 500 may interact with platform 104 to adjust the suggested dosage, recommend alternative (e.g., generic equivalent) of the initially suggested treatment/drug, etc. so that the patient's profile safety rating may be adjusted to be relatively "safe."

FIG. 5B illustrates another example GUI 520 that includes, in addition to patient identifier 501, patient's profile safety score 502, portions 504, 506 and 508, portion 522 with detailed information about an initially suggested drug including usage, the drug's associated price, patient's profile safety rating 502 mentioned above, etc.

Platform 104, by performing example method of FIGS. 2 and 3 can provide the following advantages. First, platform 104 provides an enhancement to technological platforms and tools used to assist physicians, pharmacists and healthcare providers in prescribing and administering treatments and drugs to patients. There is a wide variety of disconnected and disjointed databases of patient specific and drug specific information that are massive and very difficult, if not impossible, to parse through to deduce as much information as possible related to a patient's health conditions and/or effects of different treatments and drugs on such patient. The enhancement provided by platform 104 is the elimination of the need for physicians, pharmacists and healthcare providers to connect to individual and disconnected databases separately and extract information. This elimination reduces problems with exchange of massive amount of information and hence reduces network resource consumption. This elimination can also reduce the susceptibility of such databases to unauthorized access to patient and drug/treatment related information. Platform 104 is an all-in-one analysis tool that securely pulls every available detail about a patient, the patient's health conditions and an ordered (prescribed) treatment, analyzes the information and generates a unique and personal safety score that can provide an easy to understand information about whether providing a particular drug and a specific dosage thereof to a patient is safe or not.

Furthermore, platform 104 can improve medication safety by providing comprehensive information immediately to prescribers, physicians and pharmacists. It can make comprehensive counseling information rapidly available to consulting pharmacists and physicians. It can improve patient therapeutic response. It can reduce adverse drug reactions, drug interactions, morbidity, injury and health care costs. It fulfills OBRA-90 requirements requiring pharmacist review of patients' medication profiles, to screen prescriptions prospectively and to counsel accordingly. It can aid in meeting Joint Commission Standards for Drug Utilization Evaluation (DUE), Drug Utilization Review (DUR) and Medication Management. Platform 104 can also determine and reports cost savings attributable to dose adjustments.

Having described various examples of providing a comprehensive patient and drug providing analysis using patient and drug specific data, with reference to FIGS. 2-5, the disclosure now turns to an example system and components thereof, which may be utilized to implement terminal 102, platform 104, etc.

Figure 6:
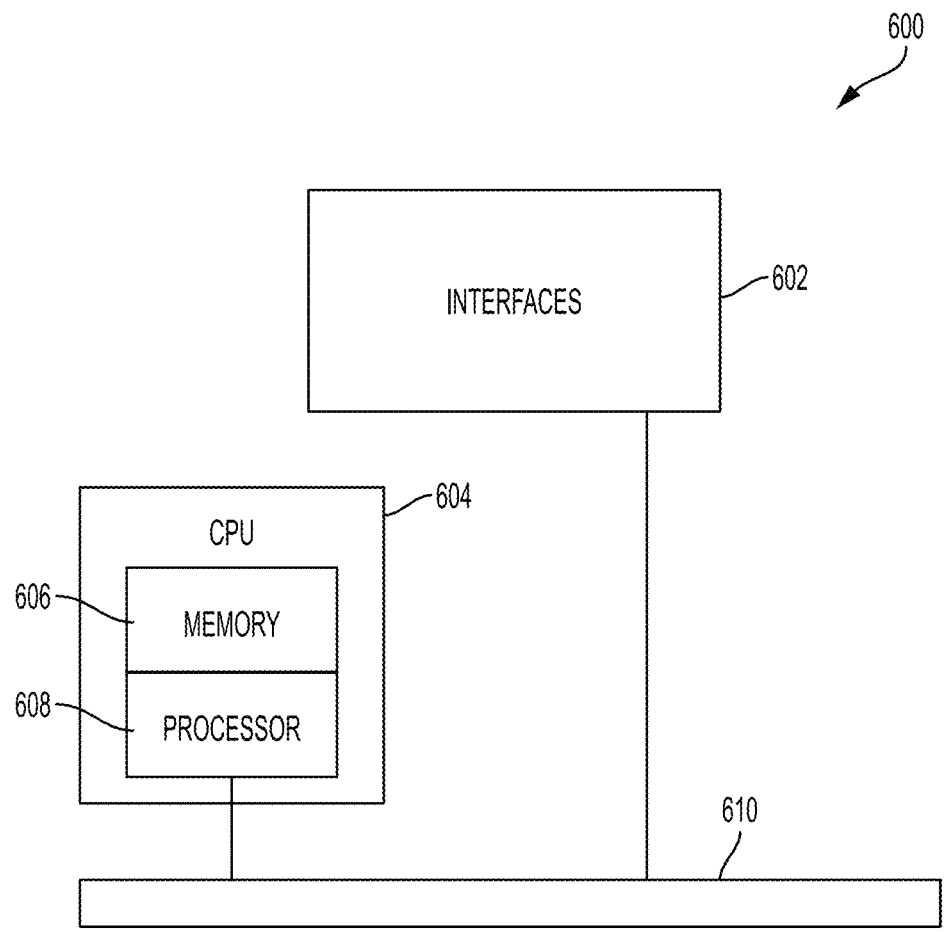
FIG. 6 illustrates an example computing device, according to an aspect of the present disclosure.

FIG. 6 illustrates an example computing device, according to an aspect of the present disclosure. Network device 600 includes a central processing unit (CPU) 604, interfaces 602, and a bus 610 (e.g., a PCI bus). When acting under the control of appropriate software or firmware, the CPU 604 is responsible for executing packet management, error detection, and/or routing functions. The CPU 604 preferably accomplishes all these functions under the control of software including an operating system and any appropriate applications software. CPU 604 may include one or more processors 608, such as a processor from the INTEL X86 family of microprocessors. In some cases, processor 608 can be specially designed hardware for controlling the operations of network device 600. In some cases, a memory 606 (e.g., non-volatile RAM, ROM, etc.) also forms part of CPU 604. However, there are many different ways in which memory could be coupled to the system.

The interfaces 602 are typically provided as modular interface cards (sometimes referred to as "line cards"). Generally, they control the sending and receiving of data packets over the network and sometimes support other peripherals used with the network device 600. Among the interfaces that may be provided are Ethernet interfaces, frame relay interfaces, cable interfaces, DSL interfaces, token ring interfaces, and the like. In addition, various very high-speed interfaces may be provided such as fast token ring interfaces, wireless interfaces, Ethernet interfaces, Gigabit Ethernet interfaces, ATM interfaces, HSSI interfaces, POS interfaces, FDDI interfaces, WIFI interfaces, 3G/4G/5G cellular interfaces, CAN BUS, LoRA, and the like. Generally, these interfaces may include ports appropriate for communication with the appropriate media. In some cases, they may also include an independent processor and, in some instances, volatile RAM. The independent processors may control such communications intensive tasks as packet switching, media control, signal processing, crypto processing, and management. By providing separate processors for the communications intensive tasks, these interfaces allow the master microprocessor 604 to efficiently perform routing computations, network diagnostics, security functions, etc.

Although the system shown in FIG. 6 is one specific network device of the present invention, it is by no means the only network device architecture on which the present invention can be implemented. For example, an architecture having a single processor that handles communications as well as routing computations, etc., is often used. Further, other types of interfaces and media could also be used with the network device 600.

Regardless of the network device's configuration, it may employ one or more memories or memory modules (including memory 606) configured to store program instructions for the general-purpose network operations and mechanisms for roaming, route optimization and routing functions described herein. The program instructions may control the operation of an operating system and/or one or more applications, for example. The memory or memories may also be configured to store tables such as mobility binding, registration, and association tables, etc. Memory 606 could also hold various software containers and virtualized execution environments and data.

The network device 600 can also include an application-specific integrated circuit (ASIC), which can be configured to perform routing and/or switching operations. The ASIC can communicate with other components in the network device 600 via the bus 610, to exchange data and signals and coordinate various types of operations by the network device 600, such as routing, switching, and/or data storage operations, for example.

For clarity of explanation, in some instances the present technology may be presented as including individual functional blocks including functional blocks comprising devices, device components, steps or routines in a method embodied in software, or combinations of hardware and software.

In some example embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

Claim language reciting "at least one of" a set indicates that one member of the set or multiple members of the set satisfy the claim. For example, claim language reciting "at least one of A and B" means A, B, or A and B.

What is claimed is:

1. A patient centric analysis platform comprising:
   memory having computer-readable instructions stored therein; and
   one or more processors configured to execute the computer-readable instructions to:
   receive, from a terminal associated with a health services provider, patient identifying information of a patient;
   receive, from the terminal, an initial treatment order for the patient;
   communicate with one or more databases having stored thereon patient specific treatment information in relation to the patient;
   retrieve the patient specific treatment information;
   analyze the initial treatment order and the patient specific treatment information of the patient to determine a patient specific safety score for each treatment included in the patient specific treatment information, yielding a plurality of patient specific safety scores for all treatments included in the patient specific treatment information;
   generate a comprehensive safety score for the patient based on the plurality of patient specific safety scores;
   modify the initial treatment order based on the comprehensive safety score to yield a modified treatment; and
   administer the modified treatment to the patient.

2. The patient centric analysis platform of claim 1, wherein the one or more processors are configured to execute the computer-readable instructions to add the plurality of patient specific safety scores to generate the comprehensive safety score.

3. The patient centric analysis platform of claim 1, wherein the plurality of patient specific safety scores include:
 a medication score;
 a therapeutic duplication score;
 a metabolic interaction score;
 a drug-disease contraindication score;
 a drug to drug interaction score;
 a renal functionality score;
 a pregnancy score;
 an allergy score;
 a serum creatinine score;
 a duration score;
 an adverse reaction score; and
 a medication abuse/misuse score.

4. The patient centric analysis platform of claim 1, wherein the one or more processors are configured to execute the computer-readable instructions to determine whether the comprehensive safety score indicates that the initial treatment order is safe.

5. The patient centric analysis platform of claim 4, wherein, when the comprehensive safety score indicates that the initial treatment order is not safe, the one or more processors are configured to execute the computer-readable instructions to modify the initial treatment order.

6. The patient centric analysis platform of claim 4, wherein the one or more processors are configured to execute the computer-readable instructions to recommend an adjustment to the initial treatment order when the comprehensive safety score indicates that the initial treatment order is not safe.

7. The patient centric analysis platform of claim 1, wherein the one or more processors are configured to execute the computer-readable instructions to receive a login request and authorize access to the patient centric administration platform prior to receiving the patient identifying information.

8. The patient centric analysis platform of claim 1, wherein the one or more processors are configured to communicate, with the comprehensive safety score, a detailed report on patient specific medical history and conditions and current medication usage of the patient.

9. A patient centric analysis method comprising:
 receiving, from a terminal associated with a health service provider, patient identifying information of a patient;
 receiving, from the terminal, an initial treatment order for the patient;
 communicating with one or more databases having stored thereon patient specific treatment information in relation to the patient;
 retrieving the patient specific treatment information;
 analyzing the initial treatment order and the patient specific treatment information of the patient to determine a patient specific safety score for each treatment included in the patient specific treatment information, yielding a plurality of patient specific safety scores for all treatments included in the patient specific treatment information;
 generating a numerical assessment comprehensive safety score for the patient based on the plurality of patient specific safety scores;
 modifying the initial treatment order based on the comprehensive safety score to yield a modified treatment; and
 administering the modified treatment to the patient.

10. The patient centric analysis method of claim 9, wherein the comprehensive safety score is generated by adding the plurality of patient specific safety scores to generate the comprehensive safety score.

11. The patient centric analysis method of claim 9, wherein the plurality of patient specific safety scores include:
 a medication score;
 a therapeutic duplication score;
 a metabolic interaction score;
 a drug-disease contraindication score;
 a drug to drug interaction score;
 a renal functionality score;
 a pregnancy score;
 an allergy score;
 a serum creatinine score;
 a duration score;
 an adverse reaction score; and
 a medication abuse/misuse score.

12. The patient centric analysis method of claim 9, wherein, when the comprehensive patient safety score indicates that the initial treatment order is not safe, the method comprises modifying the initial treatment orders.

13. The patient centric analysis method of claim 9, further comprising:
 receiving a login request; and
 authorizing access to a patient centric administration platform prior to receiving the patient identifying information.

14. The patient centric analysis method of claim 9, wherein the initial treatment is a medication.

15. One or more non-transitory computer-readable media having computer-readable instructions stored thereon, which when executed by one or more processors, cause the one or more processors to:
 receive, from a terminal associated with a health service provider, patient identifying information of a patient;
 receive, from the terminal, an initial treatment order for the patient;
 communicate with one or more databases having stored thereon patient specific treatment information in relation to the patient;
 retrieve the patient specific treatment information;
 analyze the initial treatment order and the patient specific treatment information of the patient to determine a patient specific safety score for each treatment included in the patient specific treatment information, yielding a plurality of patient specific safety scores for all treatments included in the patient specific treatment information;
 generate a comprehensive safety score for the patient based on the plurality of patient specific safety scores;
 modify the initial treatment order based on the comprehensive safety score to yield a modified treatment; and
 administer the modified treatment to the patient.

16. The one or more non-transitory computer-readable media of claim 15, wherein the execution of the computer-readable instructions further cause the one or more processors to add the plurality of patient specific safety scores to generate the comprehensive safety score.

17. The one or more non-transitory computer-readable media of claim 15, wherein the plurality of patient specific safety scores include:
 a medication score;
 a therapeutic duplication score;
 a metabolic interaction score;
 a drug-disease contraindication score;
 a drug to drug interaction score;
 a renal functionality score;

a pregnancy score;
an allergy score;
a serum creatinine score;
a duration score;
an adverse reaction score; and
a medication abuse/misuse score.

18. The patient centric analysis platform of claim 1, wherein the one or more processors are configured to modify the initial treatment order if the comprehensive safety score is equal to or greater than a threshold.

19. The patient centric analysis method of claim 9, wherein the initial treatment order is modified if the comprehensive safety score is equal to or greater than a threshold.

20. The one or more non-transitory computer-readable media of claim 15, wherein the execution of the computer-readable instructions cause the one or more processors to modify the initial treatment order if the comprehensive safety score is equal to or greater than a threshold.

* * * * *